United States Patent [19]

Griesel

[11] 4,265,118

[45] May 5, 1981

[54] URINE COLLECTING AND MEASURING INSTRUMENT

[75] Inventor: Karl-Heinz Griesel, Melsungen, Fed. Rep. of Germany

[73] Assignee: Intermedicat GmbH, Emmenbrucke, Switzerland

[21] Appl. No.: 61,257

[22] Filed: Jul. 27, 1979

[30] Foreign Application Priority Data

Aug. 24, 1978 [DE] Fed. Rep. of Germany ... 7825225[U]

[51] Int. Cl.³ .............................................. G01F 19/00
[52] U.S. Cl. ....................................... 73/427; 128/767
[58] Field of Search ................. 73/425, 427; 128/760, 128/762, 763, 767, 768, 770, 771, DIG. 24, 294, 295

[56] References Cited

U.S. PATENT DOCUMENTS

| 3,661,143 | 5/1972 | Henkin | 128/762 |
| 3,817,239 | 6/1974 | Kuntz | 128/771 X |
| 3,831,453 | 8/1974 | McWhorter | 73/427 |
| 3,871,231 | 3/1975 | Ciarico | 128/771 X |
| 3,908,656 | 9/1975 | Binard | 128/295 X |

*Primary Examiner*—James J. Gill
*Attorney, Agent, or Firm*—Merriam, Marshall & Bicknell

[57] ABSTRACT

A urine measuring instrument for receiving, collecting and measuring urine from a catheterized patient comprising a transparent, graduated container with an upper inlet and a lower outlet to which a urine bag can be connected, said container being subdivided into several side-by-side vertical chambers into the first of which the inlet communicates, all the chambers being open to one another at the top and separated from one another at the bottom by a multi-path valve, all the chambers being in communication with the container outlet through said valve, and each chamber having a scale thereon.

16 Claims, 4 Drawing Figures

URINE COLLECTING AND MEASURING INSTRUMENT

This invention provides an instrument for receiving, collecting and measuring urine from catheterized patients. The instrument consists of a transparent container with an inlet at the top and an outlet at the bottom to which a urine bag is connected.

The previously known urine measuring instruments consist of a graduated measuring container of solid, transparent material and a flexible urine bag. The urine draining from the catheter of the patient enters the measuring container via a feed tube and is collected in it. The air displaced by the urine leaves the measuring container via a germ-proof, liquid pressure-stable filter. After a certain time period, the volume of the collected urine is read on the scale of the measuring container, and then the urine is drained, through a discharge valve, which is opened, at the bottom of the measuring container, into the urine bag underneath the measuring container. The urine bag accommodates several fillings of the measuring container. In case more urine is produced than the container can hold before emptying the measuring container, the surplus amount is directly connected to the urine bag via an overflow, by bypassing the discharge valve. The urine bag and the measuring container are connected, leak-proof, with one another by means of a connector plug. When the urine bag is filled, it is replaced by a fresh one.

Through use of the previously known instruments, a number of disadvantages have become evident. Thus, the design height may be too large so that the urine bag, despite correct fastening of the instrument at the sickbed, hangs on the floor.

Previously known urine collecting instruments use a measuring container of special shape so that the scale, in order to improve the reading accuracy, is enlarged in the lower area. The upper area of the scale, on the other hand, is not enlarged so that a desired accurate reading there is often not possible.

A special problem of trans-urethral urine discharge is the prevention of infections of the urethrae. Besides inserting the non-sterile catheter, under unfavorable conditions, bacteria can migrate through the urine measuring instrument, against the flow of the draining urine, through the connecting tube and the catheter into the bladder. If urine is to be taken out of the device for testing purposes, complicated manipulations are often necessary at the point where the device has to be opened, thus leading to the danger of introducing bacteria into the apparatus. Besides, it is not always possible that the freshest urine is taken out for testing. However, testing of the freshest urine is required to obtain an accurate diagnosis of the patient's condition at the time the sample is taken.

The discharge into the urine bag, and the above-mentioned overflow, commonly merge slightly above the plug connector between the measuring container and the urine bag. While draining, the urine passes, at high speed, by the junction so that air is dragged along from the overflow and transported into the urine bag. The air which is taken along collects in the urine bag and, thus, it is impossible to fill the bag completely. Some urine bags have an additional vent to remove the air. It has to be closed by means of a bacteria-proof and leak-proof filter which is expensive for a part which is only used once.

Thus, it is clear from the above-discussed disadvantages of known urine measuring instruments, that there remained a need to design a urine measuring instrument, having a sufficient volume, which has a low design height and, at the same time, is so designed that the scale in the upper area as well, can be readily and correctly read. Also, the problem requires that measures have to be taken to prevent the counterstream bacteria migration, and the intake of air into the urine bag. Finally, there is a need for a device designed for sterile sampling of fresh urine for testing.

In order to solve one part of the described problem, the urine measuring container is subdivided into several, side-by-side, vertical chambers, into the first of which the urine delivery tube feeds. The chambers open towards one another at the top and, at the bottom, are separated from one another by a multi-path valve, connected to the outlet of the container. A scale is applied to each container chamber. To keep the design height of the measuring container low, without reducing the urine holding capacity, the design is kept relatively broad. Due to the increased width, the base surface area of the container is enlarged. This would lead to a reduced reading accuracy, since the reading error is proportional to the size of the base surface area of the measuring container. In order to keep the reading error small or to reduce it, in particular in the container upper area, as compared to the known designs, the measuring container is subdivided into several vertical chambers, which are filled consecutively. Due to this subdivision of the measuring container, and the scales individually applied to the chambers, the reading error is lowered proportionally to the reduction of the chamber base surface areas. The individual chambers are separated from the container outlet by the multi-path valve which seals each chamber individually. If the chambers were not separated, but were interconnected, the urine would be at the same level, and this would negate the effect of the partition walls with respect to accurate readability. The size of the chambers is designed according to the respective medical requirements. They may be of the same size or of varying size.

Previously, a dropper has been positioned in the upper urine feed opening to prevent counterstream bacteria migration. The dropper produces a free-fall distance between the dropper and the surface of the fluid, thus interrupting the liquid stream so that bacteria migration from the measuring container into the connecting tube to the catheter, and finally up to the patient, is interrupted. However, there have been cases where bacteria at the container lid have spread upwards to the dropper and up into the connecting tube. To prevent bacteria migration completely, the inner surface of the measuring container in the area surrounding the dropper has to be kept dry so that there is no nutrient present for the bacteria. However, the area surrounding the dropper can be moistened by back-splashing urine when the drops fall onto the surface of the liquid. To prevent back-splashing, according to the invention, a splash plate is positioned under the dropper, in the upper part of the container. The splash plate is positioned at an oblique angle to the vertical, and preferably at an acute angle. When the proper angle is chosen, the adhesive forces between drops and splash plate prevail, and the drops are retained on the splash plate. Preferably, the splash plate has an extension in the form of a substantially vertical part which projects into the first chamber of the container. As a result of this vertical part or extension, the drops run, without splashing, into the container first chamber so that the area surrounding the dropper remains dry.

A second means to prevent bacteria migration into the connecting tube which can either be used separately or in combination with the above means, comprises treating the apparatus, at a suitable location, with a germicide which kills the bacteria and thus prevents counterstream bacteria migration. In particular, treating the area surrounding the dropper with a germicide is recommended. For this purpose, a germicide such as phenols and aldehyde condensates, may be used. To enlarge the treated area and, at the same time, to increase the drop fall distance, it is preferable to manufacture the upper part of the container, substantially in the area of the feed inlet, in the shape of a dome. To prevent air, carried along by urine draining from the container, from entering and accumulating in the urine bag, and from filling it completely, a throttle area is provided in the outlet of the container in the direction of flow, behind the mouth of the exit of the multi-path valve and of an overflow. Preferably, the cross-section of the throttle area is somewhat smaller than the sum of the cross-sections of the opening covered by the multi-path valve. As a result of this design, a slight urine accumulation results in the transition between the container and the urine bag, the effect of which is that the urine runs into the overflow and seals it there against inflowing air. In an advantageous embodiment of the invention, the connector to the outlet, for connecting the urine bag between the exit of the multi-path valve and the overflow, is so designed that a T-shaped line results. In this arrangement, the mass inertia of the draining urine supplements the throttle effect at the throttle location in the container outlet so that the overflow, even more so, fills with urine.

For sterile sampling of the urine to be tested, a puncture area, for taking samples by means of a syringe, is arranged in the container wall, preferably in the front wall of the container and/or in a tube connecting the container feed inlet with the catheter. The puncture area may consist of a rubber-elastic membrane which is securely and tightly secured in place by means of a mounting. A puncture area located in the connecting tube can be advantageously provided by the transverse shank or leg of a T-shaped pipe piece or fitting inserted into the connecting tube. The provision of a puncture area has the advantage that the instrument does not have to be opened to take a sample, and thus sterility is preserved.

An embodiment of the invention is illustrated schematically in the attached drawings.

The illustrated instrument embodiment, according to the invention, combines the following functions:

Receiving and collecting urine from a catheterized patient,

Means for measuring the urine produced within a period of time, and

Means for withdrawing a urine sample.

Figure 1:
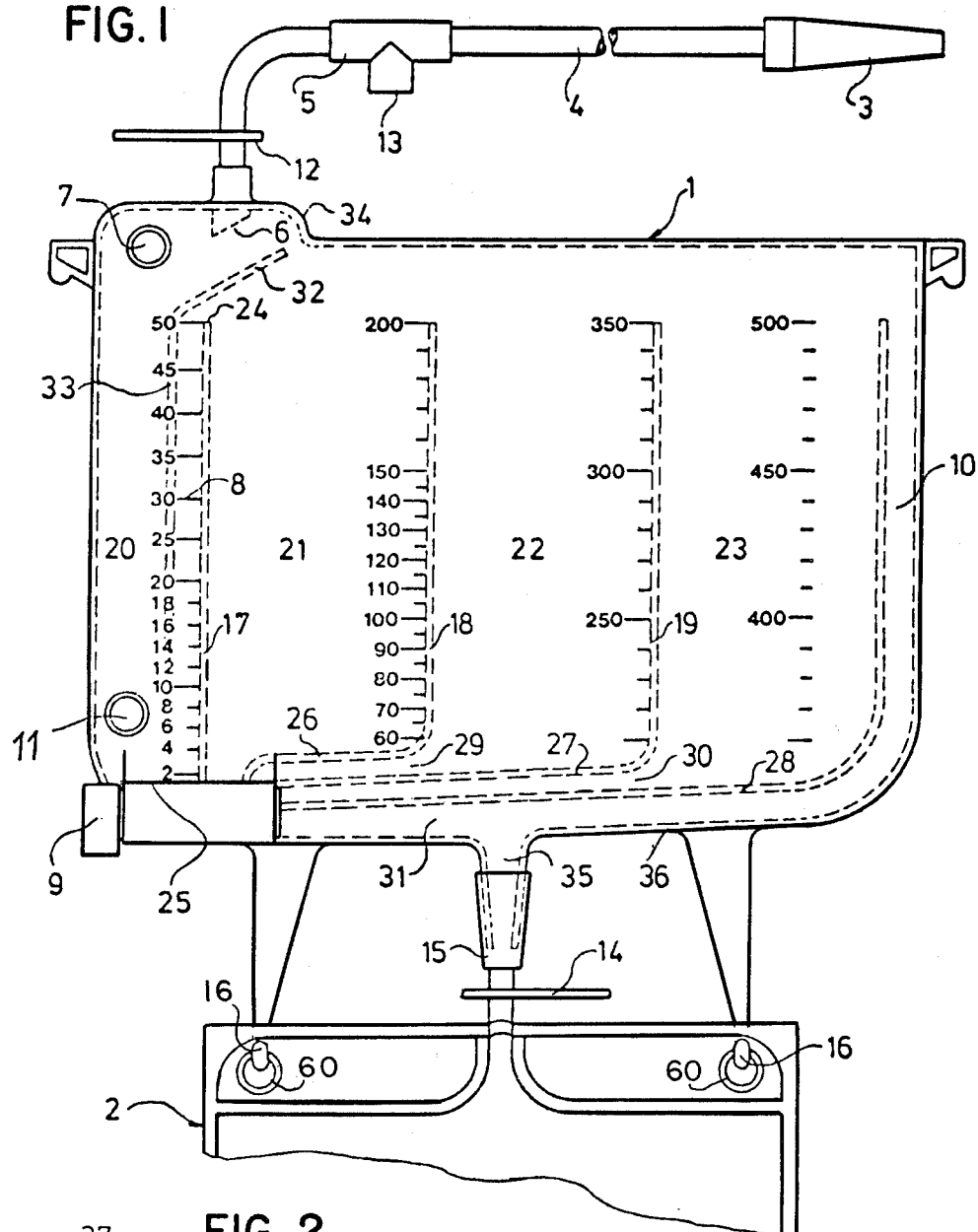
FIG. 1 is a side view of a urine measuring instrument to which a urine bag is attached.
Figure 2:
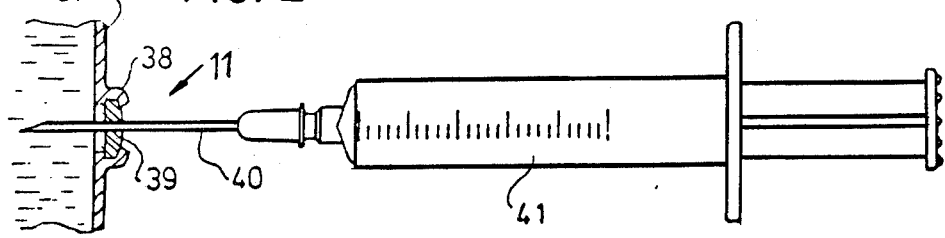
FIG. 2 is a cross-section through a puncture area for taking a sample at the measuring container by means of a commercial single-use syringe.

With reference to FIG. 1, a urine measuring instrument according to the invention includes a measuring container 1 to which an exchangeable urine bag 2 is attached. A connector 3 is connected with a corresponding counter-part of the catheter, which is not illustrated. Urine runs from the catheter via a feed tube 4, a T-shaped piece 5 for sample taking, and a dropper 6 into the measuring container 1, whereby the displaced air leaves through vent 7. The urine volume collected within a certain period of time can be read on the scales 8. A valve 9 serves to drain the urine into the urine bag 2. When the measuring container 1 is full, prior to opening of the valve 9, the excess urine runs through overflow 10 directly into the urine bag 2. Sample urine can be withdrawn at the puncture areas 11 or 13. When the urine bag 2 is full, it can be taken off hook 16, after closing clamp 14 and separation of plug connection 15, and be replaced by a new bag. The filled bag then can be emptied without opening clamp 14 and then it can be destroyed.

To keep scale reading errors to a minimum or, in particular, to reduce scale reading errors more in the upper area of the container 1, the measuring container is subdivided by several, e.g., three vertical partition walls 17, 18, and 19. The partition walls define chambers 20, 21, 22, and 23. The urine reaches chamber 20 first. When it is filled, the urine flows over the upper rim 24 into the second chamber 21 and so on. Due to the subdivision of the measuring container into several chambers, the reading error drops proportionally with reduction of the base surface areas 25, 26, 27, and 28.

For draining, the urine runs from the first two chambers 20, 21 directly, and from chambers 22, 23 through channels to valve 9 and from there, through a joint discharge 31 into the urine bag 2. The valve 9 has to seal each chamber individually. It may not be located in the joint discharge 31, since otherwise the urine, according to the principle of the communicating tubes, stands equally high in all chambers, whereby the effect of the partition walls will be negated.

A dropper 6 is positioned in the upper feed opening in the lid of the container 1. The dropper is arranged to reduce the counterstream bacteria migration into the connecting tube 4. In addition, bacteria migration is prevented by keeping dry the inner surface of the measuring container 1 in the area surrounding the dropper 6, since dry synthetic surfaces are not a nutrient for bacteria. The area surrounding the dropper 6 can be moistened by the back-splashing urine when the drops fall onto the surface of the liquid. To prevent back-splashing, a splash plate 32 is provided onto which the drops do not fall at a right angle, as onto the surface of the liquid, but at an acute angle. When the angle is properly selected, such as by a man skilled in the art, the adhesive forces between the drops and the splash plate 32 predominate, and the drop is retained on splash plate 32, from which it then runs over an adjoining vertical part 33 without spattering so that the area surrounding the dropper remains dry.

A second means used to prevent bacteria migration into the connecting tube 4 consists in the treatment with a germicide of the area surrounding dropper 6. Phenols and aldehyde condensate germicides may be used for this. To increase the germicide treated surface and the drop falling distance at the same time, the upper part of the measuring container is designed in the shape of a dome 34.

Entrance of air into the urine bag 2 is prevented, as illustrated in FIG. 1, by the arrangement of the joint discharge 31, the overflow 10, and of the plug connection 15. The inner cross-section 35 of the plug connection 15 is kept somewhat smaller than that of the opened valve 9. Due to this dimensioning, a slight urine accumulation in the plug connection 15 results. This causes the urine to run into the overflow 10 and seals it against inflowing air. In a preferred embodiment, as shown in FIG. 1, the horizontal part 36 of the overflow 10 and the joint discharge 31 form horizontal shanks, and the plug connection 15 forms the vertical shank of a big T. In this arrangement, the mass inertia of the urine stream supplements the throttle effect of the reduced cross-section 35 so that the overflow 10 fills up with urine even more easily.

For sterile sampling of urine for testing, alternative puncture areas 11 and 13 are provided. The puncture area 11 is arranged in the front wall 37 within the first chamber 20. The urine entering this chamber displaces urine already in it into the subsequent chambers so that a fresh sample can always be taken there. The puncture location 11 consists of a rubber-elastic membrane 39 which, by means of a mounting 38, is securely and tightly connected to the front wall 37. For sampling, the membrane is punctured with a tubular needle 40 and the sample is sucked into a syringe 41. When the tubular needle 40 is pulled out of the membrane 39, the punctured location closes automatically due to the inner tension of the membrane.

The puncture area 13 in the T-shaped piece 5 operates in a similar manner. When a sample is to be taken there, the clamp 12 at the feed tube 4 is closed until a sufficient volume of sample has been collected in the tube 4 or in the bladder of the patient. Both withdrawal possibilities have the advantage that the system for taking samples does not have to be opened and thus sterility remains preserved.

The urine measuring instrument is arranged so that the suspension hooks 16 of the container, the suspension loops 60 of the urine bag 2 and the container outlet, lie in the same plane.

Figure 3:
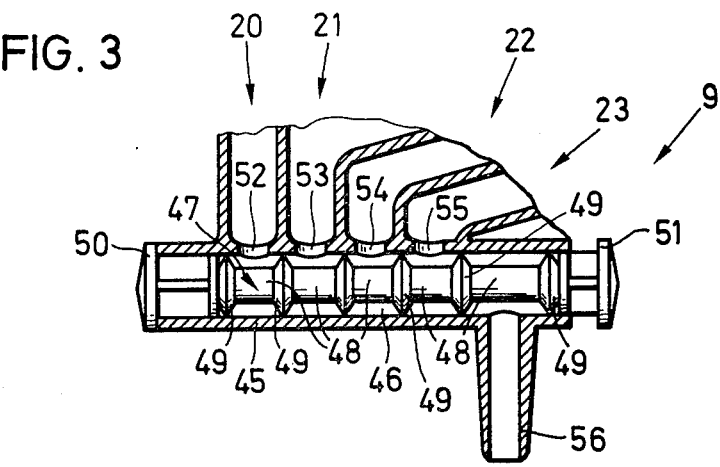
FIG. 3 is a cross-section through a valve in closed position.
Figure 4:
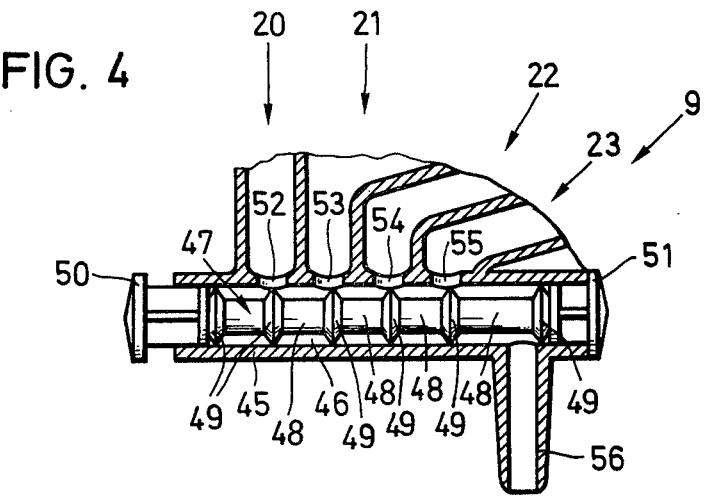
FIG. 4 is a cross-section through the valve of FIG. 3 in open position.

The valve 9 includes a housing 45 with a cylindrical bore 46 that is open at the opposite ends and houses a plunger 47. The plunger 47 is axially movable in the bore 46; it is formed cylindrically and has five peripheral grooves 48 which are limited by uninterrupted annular sealing lips 49. The plunger 47 and the sealing lips 49 may be made of rubber-elastic material. For opening and closing the valve 9, the plunger 47 can be axially moved by two press-buttons 50, 51 that are inserted in the open ends of the housing 45. Four openings 52, 53, 54, and 55 in the wall of the housing 45 connect the bore 46 or the spaces between the sealing lips 49 with the chambers 20, 21, 22, 23 of the container 1. With the valve 9 closed (FIG. 3), every opening 52, 53, 54, 55 is limited by two sealing lips 49 while with the valve 9 opened (FIG. 4), one sealing lip 49 projects into each opening in order that overflows to an outlet 56 are formed. The outlet 56 is connected to the joint discharge 31 through which urine runs into the urine bag 2 if the valve 9 is open.

What is claimed is:

1. A urine measuring instrument for receiving, collecting and measuring urine from a catheterized patient comprising a transparent, graduated container with an upper inlet and a lower outlet to which a urine bag can be connected, said container being subdivided into several side-by-side vertical chambers into the first of which the inlet communicates, all the chambers being open to one another at the top and separated from one another at the bottom by a multi-path valve, all the chambers being in communication with the container outlet through said valve, and each chamber having a scale thereon.

2. A urine measuring instrument according to claim 1 in which it is treated at a suitable location with a germicide which prevents counterstream bacterial migration.

3. A urine measuring instrument according to claim 1 including suspension hooks on the container, adapted to receive the suspension loops of a urine bag and the hooks and the connector of the outlet lie in the same plane.

4. A urine measuring instrument according to claim 1 in which the chambers are of the same size or of varying size.

5. A urine measuring instrument according to claim 1 or 4 in which the multi-path valve is located at one side of the container bottom and seals each chamber individually.

6. A urine measuring instrument according to claim 1 having a liquid throttling means in the container outlet in the direction of flow, behind the mouth of the exit of the multi-path valve and an overflow means.

7. A urine measuring instrument according to claim 6 in which the cross-section of the throttle means is smaller than that of the opened multi-path valve.

8. A urine measuring instrument according to claim 6 or 7, in which the connector at the outlet for connecting a urine bag between the exit of the multi-path valve and the overflow is arranged as a T-shaped line.

9. A urine measuring instrument according to claim 1 having a splash plate arranged in the upper part of the container beneath the upper inlet, said splash plate running at an angle to vertical to direct liquid to the first chamber.

10. A urine measuring instrument according to claim 9 in which the splash plate has a substantially vertical part which projects into the first chamber of the container.

11. A urine measuring instrument according to claim 10, in which the upper part of the container, substantially in the area of the feed, is shaped as a dome.

12. A urine measuring instrument according to claim 1 having a puncture area, arranged for sample taking by means of a syringe, located in a wall of the container.

13. A urine measuring instrument according to claim 12 in which the puncture area is in the front wall of the container close to the bottom of the first chamber.

14. A urine measuring instrument according to claim 1 having a puncture area, arranged for sample taking by means of a syringe, in a tube connecting the inlet of the container with a catheter.

15. A urine measuring instrument according to claim 12 or 14 in which the puncture area comprises a rubber-elastic membrane securely and tightly positioned in place by means of a mounting.

16. A urine measuring instrument according to claim 14 in which the puncture area is in the transverse shank of a T-shaped pipe piece in a connecting tube communicating with the container inlet.

* * * * *